United States Patent [19]

Das

[11] Patent Number: 4,771,047

[45] Date of Patent: Sep. 13, 1988

[54] BENZAZEPINE DERIVATIVES

[75] Inventor: Jagabandhu Das, Hamilton Square, N.J.

[73] Assignee: E. R. Squibb & Sons, Inc., Princeton, N.J.

[21] Appl. No.: 78,319

[22] Filed: Jul. 27, 1987

[51] Int. Cl.$^4$ .................. C07D 417/14; C07D 413/06; C07D 413/14; C07D 417/04; C07D 417/06; C07D 403/04; C07D 403/06; C07D 403/14; C07D 413/04; C07D 31/55; C07D 401/06; C07D 401/14

[52] U.S. Cl. ..................................... 514/213; 540/523

[58] Field of Search ......................... 540/523; 514/213

[56] References Cited

U.S. PATENT DOCUMENTS

| | | | |
|---|---|---|---|
| 3,312,691 | 4/1987 | Wertner et al. | 540/523 |
| 3,330,823 | 7/1967 | Bernstein et al. | 540/461 |
| 3,562,257 | 2/1971 | Kugita et al. | 540/491 |
| 3,748,321 | 7/1973 | Krapcho | 540/455 |

OTHER PUBLICATIONS

Chemical Abstracts, vol. 106 (1987), Abstracting European Patent Application, EP 205,334, published Dec. 17, 1986.

Reaction of 3-Phenylglycidic Esters IV$^1$, Reaction of Methyl 3-(4-Methoxyphenyl)glycidate with 2-Nitrophenol and Synthesis of 1,5-Benzoxazenine Derivatives, Hashiyama et al., (Chem. Pharm. Bull.)

Primary Examiner—Robert T. Bond
Attorney, Agent, or Firm—Lawrence S. Levinson; Theodore R. Furman, Jr.

[57] ABSTRACT

A new class of benzazepine derivatives having the general formula

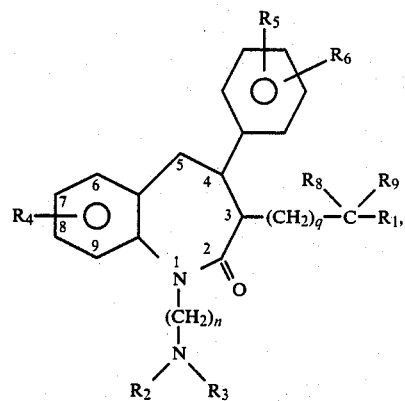

including pharmaceutically acceptable salts, are disclosed. These compounds are useful as cardiovascular agents, particularly as vasodilators.

6 Claims, No Drawings

BENZAZEPINE DERIVATIVES

FIELD OF THE INVENTION

The present invention relates to benzazepine derivatives and more particularly concerns such compounds useful as cardiovascular agents.

SUMMARY OF THE INVENTION

In accordance with the present invention a novel class of benzazepine derivatives useful, for example, as cardiovascular agents, are disclosed. These compounds have the general formula

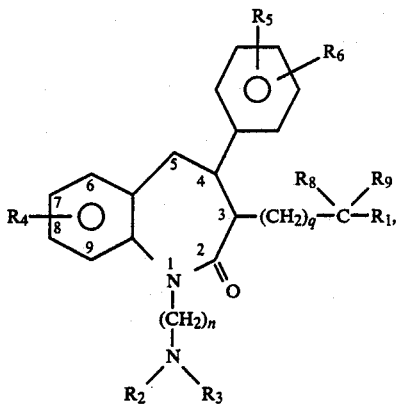

including pharmaceutically acceptable salts thereof, wherein $R_1$ is hydrogen, hydroxy, alkyl, aryl, arylalkyl or $-OR_7$;

$R_2$ and $R_3$ are each independently hydrogen, alkyl, cycloalkyl or arylalkyl, or $R_2$ and $R_3$ together with the nitrogen atom to which they are attached are pyrrolidinyl, piperidinyl, or morpholinyl;

$R_4$, $R_5$ and $R_6$ are each independently hydrogen, halogen, alkyl, alkoxy, aryloxy, arylalkoxy, diarylalkoxy, arylalkyl, cyano, hydroxy, alkanoyloxy,

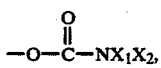

fluoro substituted alkoxy, fluoro substituted alkyl, (cycloalkyl)alkoxy, $-NO_2$, $-NX_3X_4$, $-S(O)_m$alkyl, $-S(O)_m$aryl,

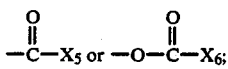

$R_7$ is alkyl, aryl or arylalkyl, $R_8$ and $R_9$ taken together are oxygen or $R_8$ is hydrogen and $R_9$ is hydroxy;

n is 2 or 3;

m is 0, 1 or 2;

q is an integer from 1 to 5;

$X_1$ and $X_2$ are each independently hydrogen, alkyl, aryl or heteroaryl, or $X_1$ and $X_2$ together with the nitrogen atom to which they are attached are pyrrolidinyl, piperidinyl or morpholinyl;

$X_3$ and $X_4$ are each independently hydrogen, alkyl, alkanoyl, arylcarbonyl, heteroarylcarbonyl, or

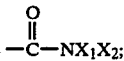

$X_5$ is hydroxy, alkoxy, aryloxy, amino, alkylamino or dialkylamino; and $X_6$ is alkyl, alkoxy or aryloxy;

with the proviso that if $R_4$ is a 7-alkyl group, it must have a tertiary carbon atom bonded to the ring.

DETAILED DESCRIPTION OF THE INVENTION

Listed below are definitions of various terms used to describe the benzazepines of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 amino ($-NH_2$), alkylamino, dialkylamino, nitro, halogen, hydroxyl, trifluoromethyl, alkyl (of 1 to 4 carbon atoms), alkoxy (of 1 to 4 carbon atoms), alkanoyloxy, carbamoyl, or carboxyl groups.

The term "alkanoyl" refers to groups having the formula

Those alkanoyl groups having 2 to 11 carbon atoms are preferred.

The term "heteroaryl" refers to an aromatic heterocyclic group having at least one heteroatom in the ring. Preferred groups are pyridinyl, pyrrolyl, imidazolyl, furyl, thienyl, or thiazolyl.

The term "cycloalkyl" refers to groups having 3, 4, 5, 6 or 7 carbon atoms.

The term "halogen" refers to fluorine, chlorine, bromine and iodine.

The terms "fluoro substituted alkyl" and "fluoro substituted alkoxy" refers to alkyl and alkoxy groups (as described above) in which one or more hydrogens have been replaced by fluorine atoms. Exemplary groups are trifluoromethyl, 2,2,2-trifluoroethyl, pentafluoroethyl, fluoromethoxy, difluoromethoxy, etc.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, citrate, succinate, benzoate, ascorbate, salicylate, methanesulfonate, benzenesulfonate, toluenesulfonate and the like.

The carbon atoms in the 3 and 4-positions of the benzazepine nucleus of the compound of formula I are asymmetric carbons. The compounds of formula I, therefore, exist in enantiomeric and diastereomeric forms and as racemic mixtures thereof. All are within the scope of this invention. It is believed that those compounds of formula I which have the 3S, 4R configuration are the most potent and are therefore preferred.

The compounds of formula I can be prepared by first reacting a 2-nitrotoluene having the formula

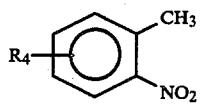

with a benzylidine malonate having the formula

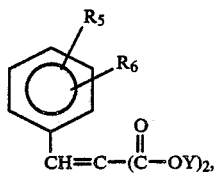

wherein Y is alkyl. The reaction can be run in a polar nonprotic solvent (e.g., dimethylformamide), in the presence of a strong base such as sodium hydride, and yields a product having the formula

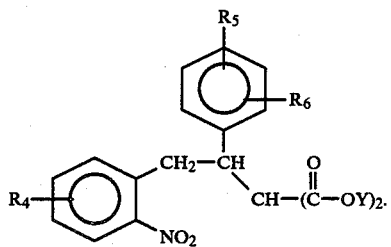

Reduction of a compound of formula IV yields the corresponding compound having the formula

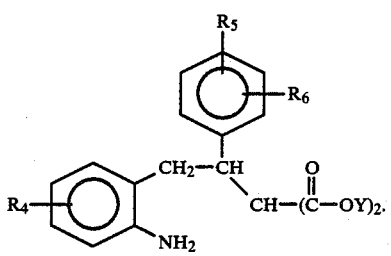

The reduction can be accomplished by catalytic hydrogenation (using, for example, palladium on charcoal as a catalyst) or using a chemical reducing agent (e.g., ferrous sulfate or stannous chloride).

Treatment of an amine of formula V with an alkali metal alkoxide (e.g., sodium methoxide) and an alcohol (e.g., methanol) yields the corresponding benzazepine having the formula

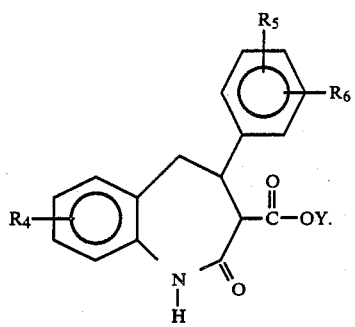

Reaction of compound VI in a solvent, e.g., dimethylformamide, in the presence of a base, e.g., sodium hydride, with bromoethylmethyl ether provides a compound having the formula

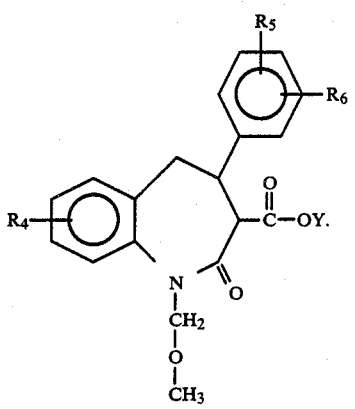

Compound VII can be reacted with a compound having the formula

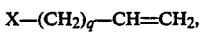

$$X-(CH_2)_q-CH=CH_2, \quad \text{VIII}$$

where X=CL, Br, I in a solvent, e.g., dimethylformamide, and in the presence of a base, e.g., sodium hydride, at low temperature to provide a compound having the formula

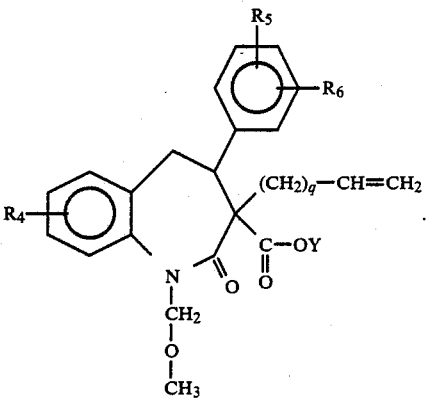

Treatment of a compound of formula IX with a strong acid, e.g., sulfuric, in the presence of anhydrous lithium bromide, provides

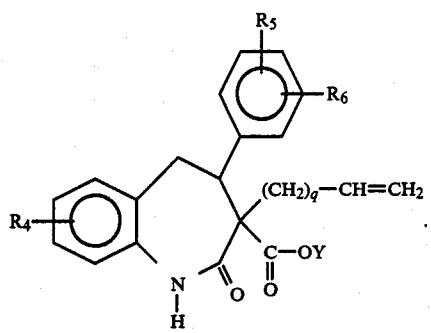

X

Compound X in a solvent, e.g., pyridine or dimethylformamide, can thereafter be reacted with lithium bromide, or lithium iodide in presence or absence of p-amino-thiophenol to obtain a diastereomeric mixture of compounds having the formulas

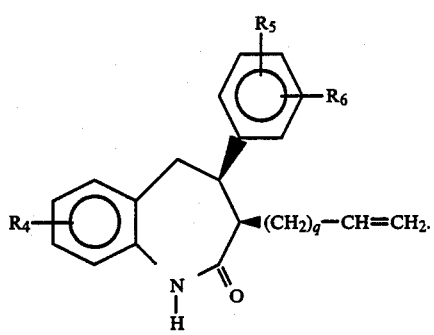

cis isomer and

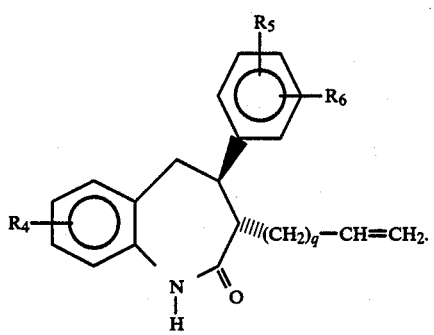

XIb trans isomer

The preferred Cis isomer is generally the predominant isomer formed during the above reaction. The isomers can be separated using art recognized techniques such as crystallization or chromatography. Alternatively, the reactions described hereinafter can be run using a diastereomeric mixture (a mixture of the compounds of formulas XIa and XIb). The isomeric mixtures can be separated into their component isomers at any point during the reaction sequence.

Reaction of the compound of formula XIa in a solvent such as tetrahydrofuran with an ethereal solution of osmium tetroxide followed by treatment with aqueous sodium bisulfite provides a compound of the formula

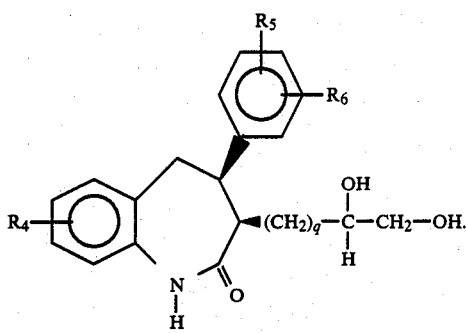

XII

Treatment of compound XII in methanol with sodium-meta-periodate in water provides a compound of the formula

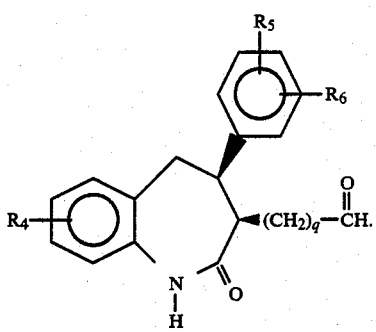

XIII

Compound XIII, in an organic solvent such as dimethylformamide, can be reacted with a compound of the formula $R_1$—Li            XIV or $R_1$—MgX           XIVa where X is halogen and $R_1$ is alkyl, aryl, arylalkyl to provide

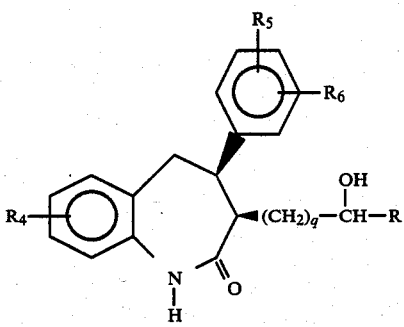

XV

Treatment of compound XV, in a solvent such as dimethylsulfoxide, with triethylamine, followed by reaction with sulfur trioxide-pyridine complex provides a compound having the formula

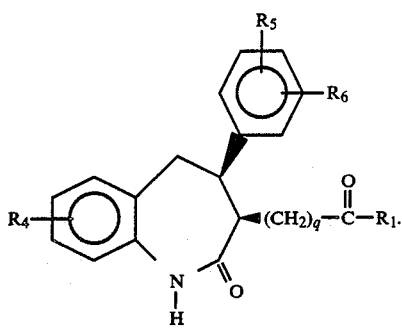

XVI

Treatment of the compound of formula XVI with a base, e.g., potassium hydrogen carbonate, or sodium hydride in the presence of a solvent, e.g., methylethylketone or dimethylformamide followed by reaction with a compound having the formula

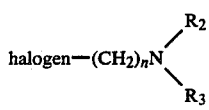 XVII yields the compounds of formula I.

Compound XV can be treated as the compound XVI above to provide compounds of formula I wherein $R_8$ is hydrogen and $R_9$ is hydroxy. Compound XIII can be treated as the compound XVI above to provide the compounds of formula I, wherein $R_1$ is hydrogen. To prepare compounds of formula I, wherein $R_1$ is —$OR_7$, compounds of formula XIII can be oxidized with a mild oxidizing agent, like silver oxide, in an aqueous base or with pyridinium dichromate in a solvent like dimethylformamide, to obtain a compound of the formula

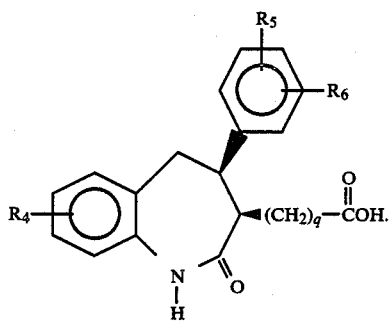

XVIII

Compound XVIII can be esterified with etheral diazomethane or with an alcohol of the formula $R_7OH$ in the presence of an anhydrous acid like hydrochloric acid, sulfuric acid or amberlyst acid exchange resin to obtain a compound of the formula

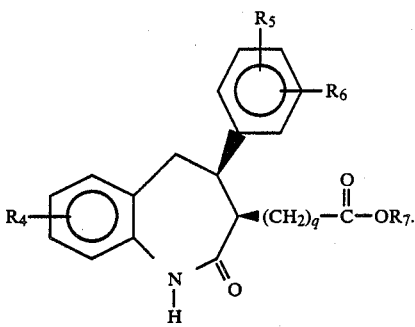

XIX

Compound XIX can be treated as the Compound XVI above to provide the compounds of formula I, wherein $R_1$ is —$OR_7$. Compounds of formula I wherein $R_1$ is —OH can be prepared by reacting compounds of formula I wherein $R_1$ is —$OR_7$ with an aqueous acid like hydrochloric acid or sulfuric acid or with an aqueous base like lithium hydroxide or sodium hydroxide in an organic solvent like tetrahydrofuran.

The resolved enantiomers of the compounds of this invention can be prepared by first hydrolyzing a compound of formula VI to obtain the corresponding carboxylic acid having the formula

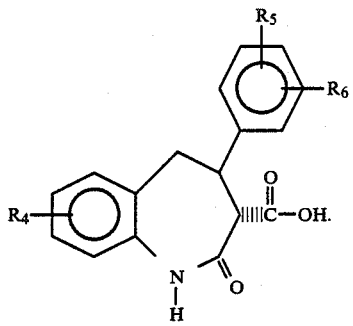

XX

The hydrolysis can be accomplished, for example, by treating a compound of formula VI with an alkali metal hydroxide in an alcohol (e.g., potassium hydroxide in methanol).

A carboxylic acid of formula XX can be resolved using a chiral amine. Reaction of the acid and amine in an appropriate solvent yields the diastereomeric salts which can be separated using conventional techniques such as crystallization. Regeneration of the carboxylic acid from the pure diastereomeric salt followed by esterification yields the desired nonracemic form of a compound of formula VI. Alternatively, compounds of formula VI can be generated directly from the diastereomeric salts by treatment with an alkyl halide in dimethylformamide in the presence of an inorganic base (e.g., potassium bicarbonate). This nonracemic compound can be converted to the corresponding nonracemic product of formula I via the nonracemic form of intermediates of formulas VII and IX-XVI using the procedures described above.

Alternatively, the resolved enantiomers of the compounds of this invention can be prepared by the reaction of the various forms of formula I, prepared above, with a chiral carboxylic acid in an appropriate solvent. The resulting diastereomeric salts can be separated by recrystallization.

In the reactions described above for preparing the compounds of this invention, it may be necessary to protect reactive substituents (e.g., hydroxy and amino) from involvement in the reactions. Protection of the substituents, and the necessary deprotection, can be accomplished using standard techniques.

Preferred are those compounds of formula I wherein $R_1$ is alkyl;

$R_2$ and $R_3$ are each methyl or $R_2$ is hydrogen and $R_3$ is methyl $R_4$ is trifluoromethyl (especially 7-trifluoromethyl and 6-trifluoromethyl);

$R_5$ is 4-methoxy;

$R_6$ is hydrogen;

$R_8$ and $R_9$ taken together are oxygen; and, q is 1 or 2.

The compounds of formula I and the pharmaceutically acceptable salts thereof are useful as cardiovascular agents. These compounds act as vasodilators and are especially useful as anti-hypertensive agents. By the administration of a composition containing one (or a combination) of the compounds of this invention the blood pressure of a hypertensive mammalian (e.g., human) host is reduced. Daily doses of about 0.1 to 100 mg per kilogram of body weight per day, preferably about 1 to about 50 mg per kilogram per day, are appropriate to reduce blood pressure, and can be administered in single or divided doses. The substance is preferably administered orally, but parenteral routes such as the subcutaneous, intramuscular, or intravenous routes can also be employed.

As a result of the vasodilating activity of the compounds of formula I, it is believed that such compounds in addition to being anti-hypertensives may also be useful as anti-arrhythmic agents, as anti-anginal agents, as anti-fibrillatory agents, as anti-asthmatic agents, and in limiting myocardial infarction.

The compounds of this invention can also be formulated in combination with a diuretic or an angiotensin converting enzyme inhibitor. Suitable diuretics include the thiazide diuretics such as hydrochlorothiazide and bendroflumethiazide and suitable angiotensin converting enzyme inhibitors include captopril.

The present invention will be further described by reference to the following examples, however, it is not meant to be limited by the details described therein.

EXAMPLE 1

(cis)-1-[Dimethylamino)ethyl]-1,3,4,5-tetrahydro-4-(4-methoxyphenyl)-3-(2-oxopropyl)-7-(trifluoromethyl)-2H-1-benzazepin-2-one,monohydrochloride.

A.

[2-(5-Trifluoromethyl-2-nitrophenyl)-1-(4-methoxyphenyl)ethyl]propanedioic acid, dimethyl ester To a 2 liter three-neck flask (under nitrogen) was added 67.0 g. (0.293 mol) of dimethyl-p-methoxy-benzylidene malonate and 450 ml of dimethylformamide. The stirred solution was treated with 18.7 g. (0.39 mol) of 50% sodium hydride dispersion. The mixture was treated dropwise with a solution of 60.5 g. (0.293 mol) of 2-nitro-5-(trifluoromethyl)-toluene in 50 ml of dimethylformamide over a period of 1 hour while maintaining the temperature at 28°-32° C. (near the end of the addition, the temperature rose to 38° C. and was rapidly cooled to 30° C.). The mixture was stirred for 4 hours at room temperature, cooled, treated portionwise with 25 ml of acetic acid and poured onto 2.5 liters of ice-water. The mixture was extracted with 250 ml dichloromethane (3 times). The organic phases were combined, washed with 500 ml of water (3 times), dried (magnesium sulfate), filtered and the solvent evaporated to give 126 g of a pale brown semi-solid. The latter was dissolved in 270 ml of methanol, cooled and filtered to give 72.8 g. of a pale yellow product, melting point 110°-112° C. $R_f$=0.74 (1:1 ethyl acetate-hexane). A sample recrystallized from methanol, melted at 111°-113°.

Analysis calc'd for $C_{21}H_{20}NF_3O_7$: C, 55.39; H, 4.43; N, 3.08; F, 12.52; Found: C, 56.08; H, 4.70; N, 2.96; F, 12.09.

B.

[2-(5-Trifluoromethyl-2-aminophenyl)-1-(4-methoxyphenyl)ethyl]propanedioic acid, dimethyl ester A suspension of 25.0 g (0.055 mol) of [2-(5-trifluoromethyl-2-nitrophenyl)-1-(4-methoxyphenyl)ethyl]propanedioic acid, dimethyl ester in 200 ml of methanol was treated with a cold suspension of 2.5 g of 5% palladium on charcoal in 50 ml of methanol (under nitrogen) and placed on the Parr apparatus at 58 psi of hydrogen. After 30 minutes, the mixture was heated to 50°-55° C. for 1 hour to assure that all of the nitro compound had dissolved. The mixture was removed from the Parr and allowed to stand at room temperature overnight. The flask was heated to dissolve the crystallized product, and the hot solution was filtered through Celite (under nitrogen) and washed with hot methanol. The colorless filtrate was concentrated on a rotary evaporator to give 22.2 g of a nearly colorless solid. The latter was triturated with 100 ml of hexane and then with 50 ml of hexane. The solvent was decanted and the entrained solvent removed on a rotary evaporator to give 21.3 g of product, melting point 124°-127° C. $R_f$=0.62 (1:1 ethyl acetate-hexane). A sample of this material, after crystallization from methanol, melted at 125°-127° C.

Analysis calc'd for $C_{21}H_{22}NF_3O_5$: C, 59.29; H, 5.21; N, 3.29; F, 13.40; Found: C, 59.48; H, 5.26; N, 3.16; F, 13.43.

C.

7-(Trifluoromethyl)-1,3,4,5-tetrahydro-3-(methoxycarbonyl)-4-(4-methoxyphenyl)-2H-1-benzazepin-2one A stirred solution of the title B compound (20.0 g, 0.047 mol) in 200 ml of methanol was treated with 13.3 ml of 25% sodium methoxide in methanol and heated to reflux for 2.75 hours. The reaction mixture was cooled in ice-water and treated with 70 ml of 1N hydrochloric acid solution. The precipitated tan solid was filtered, washed with water, and air dried to obtain 19 g of a pale yellow foam-like material. The latter was suspended in 30 ml of isopropylalcohol, allowed to stand for 1 hour, filtered and washed with isopropylalcohol and hexane to obtain 13.64 g of the title C compound, m.p. 161°-163°.

Analysis calc'd for $C_{20}H_{18}NF_3O_4$: C, 61.07; H, 4.61; N, 3.56; F, 14.49; Found: C, 61.26; H, 4.62; N, 3.41; F, 14.21.

D.

7-(Trifluoromethyl)-1,3,4,5-tetrahydro-3-methoxycarbonyl)-1-(methoxymethyl)-4-(4-methoxyphenyl)-2H-1-benzazepin-2-one To a suspension of sodium hydride (360 mg, 7.5 mmole, 50% oil dispersion/prewashed with dry ether several times) in dry dimethylformamide (30 ml), cooled at 0°–5° C. was added a solution of the title C compound (1.9 g, 5 mmole) in dry dimethylformamide (15 ml) dropwise. The mixture was stirred for an additional 20 minutes at 0°–5° C., whereupon bromomethylmethyl ether (800 μl, 10 mmole) was added dropwise. After 1 hour at 0°–5° C. excess sodium hydride was destroyed by the addition of water. The mixture was diluted with ether and washed with water. The aqueous layer was extracted three times with ether and the combined ether extracts were dried over magnesium sulfate and concentrated. The crude oily residue was flash chromatographed to obtain 1.67 g of the title D compound as a colorless oil.

E.
3-Allyl-1,3,4,5-tetrahydro-3-(methoxycarbonyl)-1-(methoxymethyl)-4-(4-methoxyphenyl)-7-(trifluoromethyl)-2H-1-benzazepin-2-one To a suspension of sodium hydride (384 mg, 8 mole, 50% oil dispersion) in dry dimethylformamide (35 ml), cooled in an ice-water bath, was added a solution of the title D compound (917 mg, 21 mmole) in dimethylformamide (8 ml) with stirring. After 30 minutes, allyl bromide (1.5 ml) was added in one portion. The mixture was allowed to stand at 0°–5° C. for 3 additional hours, whereupon excess hydride was destroyed by the addition of water. The mixture was diluted with ether and washed with water. The aqueous layer was extracted three times with ether, and the combined ether extracts were dried over magnesium sulfate, and concentrated. The crude residue was flash chromatographed to obtain 905 mg of the title E compound as a white crystalline material.

F.
3-Allyl-1,3,4,5-tetrahydro-3-(methoxycarbonyl)-1-4(methoxyphenyl)-7-(trifluoromethyl)-2H-1-benzazepin-2-one Concentrated sulfuric acid (8 ml) and anhydrous lithium bromide (720 mg, 8 mmole) were added to a suspension of the title E compound (905 mg, 1.9 mmole) in methanol (40 ml) with stirring. The reaction mixture was heated under reflux for 9 hours, and then allowed to stand overnight at room temperature. The acid was carefully neutralized by the addition of saturated sodium hydrogen carbonate solution and the reaction mixture was extracted three times with ethyl acetate. The combined organic layers were dried over magnesium sulfate and concentrated giving 858 mg of the title F compound as an off-white solid.

G.
(Cis)-3-Allyl-1,3,4,5-tetrahydro-4-(methoxyphenyl)-7-(trifluoromethyl)-2H-1-benzazepin-2-one.

Lithium iodide (13.75 g,102.6 mmole) was added to the title F compound 42.94 g, 44 mmole) in 300 ml of pyridine containing 1–2% of water. The reaction mixture was heated under reflux for 2 days. Pyridine was removed by distillation in vacuo and the solid residue was dissolved in chloroform, washed four times with 1N hydrochloric acid solution and saturated sodium chloride solution, dried over anyhydrous magnesium sulfate, filtered and concentrated. The crude reside was triturated with methanol to obtain 19.87 g of the title G compound as a white solid.

H.
(Cis)-7-(Trifluoromethyl)-1,3,4,5-tetrahydro-3-(2,3-dihydroxypropyl)-4-(4-methoxyphenyl)-2H-1-benzapein-2-one To a solution of the title G compound (2.6 g, 7 mmole) in tetrahydrofuran (40 ml) was added with stirring 300 μl of an ethereal solution of osmium tetroxide (1 g/10 ml of ether). A solution of N-methylmorpholine-N-oxide (1.25 g, 9 mmole) in water (5 ml) was added to the mixture dropwise. The solution was stirred at room temperature overnight, whereupon an aqueous sodium bisulfite solution was added and the reaction mixture was stirred for an additional 10 minutes to decompose the osmium tetroxide. The solution was diluted with ethyl acetate. The ethyl acetate layer was separated and the aqueous layer was extracted twice with ethyl acetate. The combined organic extract was dried over anhydrous magnesium sulfate and concentrated to obtain 2.75 g of the title H compound as a white crystalline solid.

I.
(Cis)-7-(Trifluoromethyl)-1,3,4,5-tetrahydro-3-(2-oxoethyl)-4-(4-methoxyphenyl)-2H-1-benazaepin-2-one To a solution of the title H compound (2.75 g, 7 mmole) in methanol (35 ml), cooled in an ice-bath, was added sodium-meta-periodate (3 g, 14 mmole) in water (15 ml), dropwise with stirring. The mixture was allowed to stir at 0° C. for 30 minutes, whereupon it was diluted with water and extracted with ethyl acetate. The combined organic extract was dried over anhydrous magnesium sulfate and concentrated. The residue was flash chromatographed using 20–50% ethyl acetate in hexane to obtain 2.05 g of the title I compound as a white crystalline solid.

J.
(Cis)-7-(Trifluoromethyl)-1,3,4,5-tetrahydro-3-(2-hydroxypropyl)-4-(4-methoxyphenyl)-2H-1-benzazepin-2-one A 1.6M solution of methyllithium in ether (15 ml, 21 mmole, 2.5 eq) was added dropwise and with stirring to a solution of the title I compound (1.12 g, 3 mmole) in dry dimethylformamide (20 ml) at 0° C. Stirring was continued at 0° C. for 5 hours, whereupon excess methyllithium was destroyed by the careful addition of 2N aqueous hydrochloric acid solution. The aqueous layer was extracted 3 times with ethyl acetate, and the combined organic extract was dried over anhydrous magnesium sulfate and concentrated giving 997 mg of the title J compound.

K.
(Cis)-7-(Trisfluoromethyl)-1,3,4,5-tetrahydro-3-(2-oxopropyl)-4-(4-methoxyphenyl)-2H-1-benzazepin-2-one To a solution of the title J compound (997 mg, 2.56 mmole) in dimethylsulfoxide (20 ml) was added, with stirring, distilled triethylamine (1 ml, 7 mmole). Sulfur trioxide-pyridine complex (2.06 g, 13 mmole) was added in small portions and the mixture was stirred at room temperature for 6 hours. Ethyl acetate was now added, and the solution was washed 4 times with water. The aqueous wash was extracted with ethyl acetate and the combined organic extract was dried over anhydrous magnesium sulfate and concentrated. The residue was further dried in vacuo and then treated with ether to obtain a white precipitate. The precipitate was collected by filtration and washed (2:1 ether: hexane) to provide 883 mg of the title K compound.

L. (Cis)-1-[2-(Dimethylamino)ethyl]-1,3,4,5-tetrahydro-4-(4-methoxyphenyl)-3-(2-oxopropyl)-7-(trifluoromethyl)-2H-1-benzazepin-2-one, monohydrochloride To a slurry of hexane washed 60% sodium hydride (0.158 g, 3.94 mmole, 2 eq) in dry dimethylformamide (12 ml) was added the title K compound (770 mg, 1.97 mmole) with stirring. After stirring at room temperature for 45 minutes, a 2.15M solution of N,N-dimethyl-2-chloroethylamine in toluene (4.6 ml, 9.84 mmole, 5 eq) was added, and the mixture was heated at 80° C. for 5.5 hours. The cooled reaction mixture was quenched with addition of water, and was made basic with 50% sodium hydroxide. It was extracted 3 times with ethyl acetate. The combined organic extract was dried over anhydrous magnesium sulfate and concentrated. The crude dark-yellow oil was flash chromatographed on a silical gel column to obtain the free amine which was dissolved in ethyl ether, filtered and treated with etheral hydrogen chloride. The resulting white precipitate was collected by filtration, washed with ethyl ether/acetone, and dried in vacuo, yielding 340 mg of the title compound as a white solid.

Analysis calc'd for $C_{25}H_{30}N_2ClF_3O_3.0.7M\ H_2O$: C, 58.71; H, 6.19; N, 5.47; Cl, 6.93; F, 11.15; Found: C, 58.71; H, 6.09; N, 5.42; Cl, 7.22; F, 11.18.

EXAMPLES 2 to 25

Following the procedures described above and as outlined in Example 1, the following additional compounds within the scope of the present invention can be made.

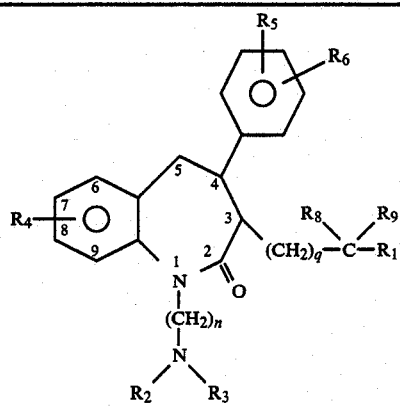

| Ex. No. | $R_1$ | q | $R_2$ | $R_3$ | $R_4$ | $R_5$ | $R_6$ | n |
|---|---|---|---|---|---|---|---|---|
| 2 | —H | 1 | —$CH_3$ | —$CH_3$ | 7-$CF_3$ | 4-$OCH_3$ | —H | 2 |
| 3 | —OH | 1 | —$CH_3$ | —$CH_3$ | 7-$CF_3$ | 4-$OCH_3$ | —H | 3 |
| 4 | —OH | 2 | —$CH_3$ | —$CH_3$ | 6-$CF_3$ | 4-$OCH_3$ | —H | 2 |
| 5 | —$C_2H_5$ | 1 | —$CH_3$ | —$CH_3$ | 7-$CF_3$ | 4-$OCH_3$ | —H | 2 |
| 6 | 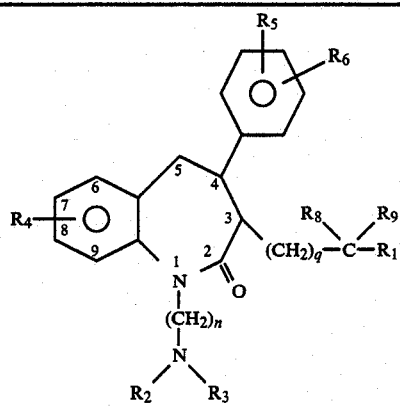 phenyl | 2 | —$CH_3$ | —$CH_3$ | 7-$CF_3$ | 4-$OCH_3$ | —H | 2 |
| 7 | —$CH_3$ | 2 |  | | 7-$CF_3$ | 4-$OCH_3$ | —H | 2 |
| 8 | —$CH_3$ | 2 | 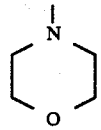 | | 7-$CF_3$ | 4-$OCH_3$ | —H | 3 |
| 9 | —$C_2H_5$ | 2 |  | | 7-$CF_3$ | 4-$OCH_3$ | —H | 2 |
| 10 | 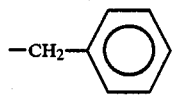 —$CH_2$-phenyl | 1 | —$CH_3$ | —$CH_3$ | 7-$CF_3$ | 4-$OCH_3$ | —H | 2 |

-continued

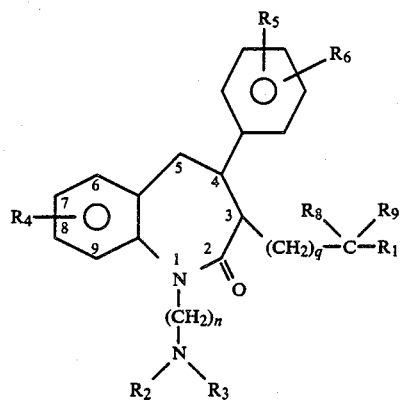

| Ex. No. | R₁ | q | R₂ | R₃ | R₄ | R₅ | R₆ | n |
|---|---|---|---|---|---|---|---|---|
| 11 | $-(CH_2)_2-\text{Ph}$ | 1 | $-CH_3$ | $-CH_3$ | 7-$CF_3$ | 4-$OCH_3$ | $-H$ | 2 |
| 12 | $-OCH_3$ | 1 | $-CH_3$ | $-CH_3$ | 7-$CF_3$ | 4-$OCH_3$ | $-H$ | 2 |
| 13 | $-OCH_2CH_3$ | 2 | $-CH_3$ | $-CH_3$ | 7-$CF_3$ | 4-$OCH_3$ | $-H$ | 2 |
| 14 | $-H$ | 1 | $-CH_3$ | $-CH_3$ | 7-Cl | 3-C≡N | 4-$OCH_3$ | 2 |
| 15 | $-CH_3$ | 2 | $-CH_3$ | $-CH_2-\text{Ph}$ | 6-$CF_3$ | 4-Br | $-H$ | 3 |
| 16 | $-OCH_2-\text{Ph}$ | 1 | $-CH_3$ | $-CH_3$ | 6-$NO_2$ | 4-O-C(=O)-$NH_2$ | 3-$CH_3$ | 2 |
| 17 | $-CH_3$ | 2 | $-CH_3$ | $-CH_3$ | 7-$NO_2$ | 4-$SO_2CH_3$ | $-H$ | 3 |
| 18 | $-C_2H_5$ | 1 | $-H$ | $-CH_3$ | 7-$CF_3$ | 4-$OCH_3$ | $-H$ | 2 |
| 19 | $-CH_3$ | 1 | $-H$ | $-CH_2-\text{Ph}$ | 6-Cl | 4-$OCH_3$ | $-H$ | 2 |
| 20 | $-O-\text{Ph}$ | 2 | $-H$ | $-CH_3$ | 6-$CF_3$ | 4-$OCH_3$ | $-H$ | 3 |
| 21 | $-OCH_3$ | 1 | $-H$ | $-CH_3$ | 7-$CF_3$ | 4-$OCH_3$ | $-H$ | 2 |
| 22 | $-OCH_2CH_3$ | 1 | $-H$ | $-CH_3$ | 7-$CF_3$ | 4-$OCH_3$ | $-H$ | 3 |
| 23 | $-CH_3$ | 2 | $-H$ | $-CH_3$ | 6-$CF_3$ | 4-$OCH_3$ | $-H$ | 2 |
| 24 | $-CH_3$ | 1 | $-H$ | $-CH_3$ | 7-$CF_3$ | 4-$OCH_3$ | $-H$ | 3 |
| 25 | $-CH_3$ | 2 | $-H$ | $-CH_3$ | 7-Cl | 4-$OCH_3$ | $-H$ | 2 |

What is claimed is:
1. A compound having the formula

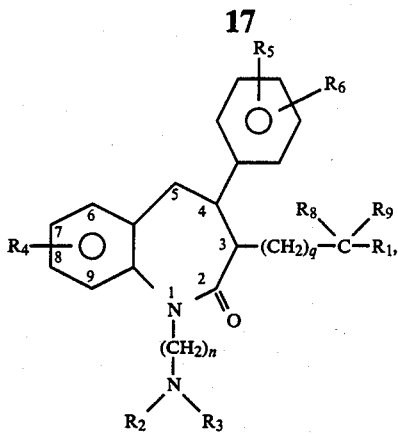

including pharmaceutically acceptable salts thereof, wherein
  $R_1$ is hydrogen, hydroxy, alkyl, aryl, arylalkyl or $-OR_7$;
  $R_2$ and $R_3$ are each independently hydrogen, alkyl, cycloalkyl or arylalkyl, or $R_2$ and $R_3$ together with the nitrogen atom to which they are attached are pyrrolidinyl, piperidinyl, or morpholinyl;
  $R_4$, $R_5$ and $R_6$ are each independently hydrogen, halogen, alkyl, alkoxy, aryloxy, arylalkoxy, diarylalkoxy, arylalkyl, cyano, hydroxy, alkanoyloxy,

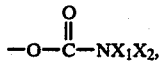

fluoro substituted alkoxy, fluoro substituted alkyl, (cycloalkyl)alkoxy, $-NO_2$, $-NX_3X_4$, $-S(O)_m$alkyl, $-S(O)_m$aryl,

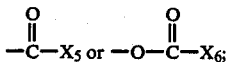

$R_7$ is alkyl, aryl or arylalkyl;
  $R_8$ and $R_9$ taken together are oxygen or
  $R_8$ is hydrogen and $R_9$ is hydroxy;
  n is 2 or 3;
  m is 0, 1 or 2;
  q is an integer from 1 to 5;
  $X_1$ and $X_2$ are each independently hydrogen, alkyl, aryl or heteroaryl, or $X_1$ and $X_2$ together with the nitrogen atom to which they are attached are pyrrolidinyl, piperidinyl or morpholinyl;
  $X_3$ and $X_4$ are each independently hydrogen, alkyl, alkanoyl, arylcarbonyl, heteroarylcarbonyl, or

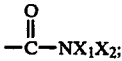

$X_5$ is hydroxy, alkoxy, aryloxy, amino, alkylamino or dialkylamino; and
  $X_6$ is alkyl, alkoxy or aryloxy; with the proviso that if $R_4$ is a 7-alkyl group, it must have a tertiary carbon atoms bonded to the ring;
and further wherein
  the terms "alkyl" and "alkoxy", by themselves or as part of another group, refer to both straight and branched chain groups having 1 to 10 carbon atoms;

the term "alkenyl", by itself or as part of another group, refers to both straight and branched chain groups having 2 to 10 carbon atoms;
the term "aryl", by itself or as part of another group, refers to phenyl and phenyl substituted with 1, 2 or 3 groups independently selected from amino, alkylamino, dialkylamino, nitro, halogen, hydroxyl, trifluoromethyl, alkyl of 1 to 4 carbon atoms, alkoxy of 1 to 4 carbon atoms, alkanoyloxy, carbamoyl, or carboxyl;
the term "alkanoyl", by itself or as part of another group, refers to groups having the formula

having 2 to 11 carbon atoms;
the term "heteroaryl" refers to pyridinyl, pyrrolyl, imidazolyl, furyl, thienyl and thiazolyl;
the term "cycloalkyl" refers to groups having 3, 4, 5, 6 or 7 carbon atoms; and,
the terms "fluoro substituted alkyl" and "fluoro substituted alkoxy", by themselves or as part of another group, refer to said alkyl and said alkoxy groups in which one or more hydrogens have been replaced by fluorine atoms.

2. A compound of claim 1 wherein
  $R_1$ is alkyl;
  $R_2$ and $R_3$ are each methyl or $R_2$ is hydrogen and $R_3$ is methyl
  $R_4$ is trifluoromethyl (especially 7-trifluoromethyl and 6-trifluoromethyl);
  $R_5$ is 4-methoxy;
  $R_6$ is hydrogen;
  $R_8$ and $R_9$ taken together are oxygen; and,
  q is 1 or 2.

3. A compound of claim 1 wherein
  $R_1$ is methyl;
  $R_2$ and $R_3$ are each methyl;
  $R_4$ is 7-trifluoromethyl;
  $R_5$ is 4-methoxy;
  $R_6$ is hydrogen;
  $R_8$ and $R_9$ taken together and oxygen;
  n is 2; and
  q is 1.

4. A compound of claim 1 having the name (Cis)-1-[Dimethylamino)ethyl]-1,3,4,5-tetrahydro-4-(4-methoxyphenyl)-3-(2-oxopropyl)-7-(trifluoromethyl)-2H-1-benzazepin-2-one, monohydrochloride.

5. A composition useful in reducing blood pressure comprising a pharmaceutically acceptable carrier and an anti-hypertensively effective amount of a compound or pharmaceutically acceptable salt thereof of the formula

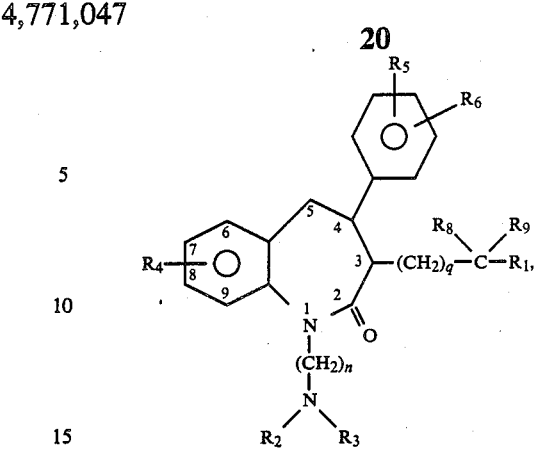
wherein $R_1$, $R_2$, $R_3$, $R_4$, $R_5$, $R_6$, $R_8$ and $R_9$, n and q are as defined in claim 1.
6. A method of reducing blood pressure in a mammal comprising administering an effective amount of the composition of claim 5.
* * * * *